United States Patent [19]

Schmidt et al.

[11] Patent Number: 4,724,141

[45] Date of Patent: Feb. 9, 1988

[54] PREPARATION OF SOLID MEDICAMENT FORMULATION CONTAINING NITRENDIPINE

[75] Inventors: Wolfgang Schmidt; Bernhard Streuff; Manfred Winter, all of Cologne, Fed. Rep. of Germany

[73] Assignee: Bayer Aktiengesellschaft, Leverkusen, Fed. Rep. of Germany

[21] Appl. No.: 772,828

[22] Filed: Sep. 5, 1985

[30] Foreign Application Priority Data

Sep. 11, 1984 [DE] Fed. Rep. of Germany ....... 3433239

[51] Int. Cl.⁴ ..................... A61K 31/44; A61K 31/79
[52] U.S. Cl. ...................................... 424/80; 514/356
[58] Field of Search ........................... 424/80; 514/356

[56] References Cited

U.S. PATENT DOCUMENTS

| | | | |
|---|---|---|---|
| 4,237,137 | 12/1980 | Tacke et al. | 514/356 |
| 4,537,898 | 8/1985 | Hoff et al. | 514/356 |
| 4,582,840 | 4/1986 | Gerthoff et al. | 514/356 |

FOREIGN PATENT DOCUMENTS

| | | |
|---|---|---|
| 3142853 | 5/1983 | Fed. Rep. of Germany . |
| 55-47615 | 4/1980 | Japan . |

Primary Examiner—Allen J. Robinson
Attorney, Agent, or Firm—Sprung Horn Kramer & Woods

[57] ABSTRACT

A solid medicament formulation comprising 1 part by weight of crystalline nitrendipine, 0.5–1 part by weight of polyvinylpyrrolidone, 0.05–0.5 part by weight of sodium lauryl-sulphate, 1–6 parts by weight of corn starch, 0.5–4 parts by weight of microcrystalline cellulose, 0–5 parts by weight of lactose and 0.01–0.05 parts by weight of magnesium stearate. Such small size formulation has a high bioavailability.

3 Claims, No Drawings

PREPARATION OF SOLID MEDICAMENT FORMULATION CONTAINING NITRENDIPINE

The invention relates to a particular solid medicament formulation which is easily absorbed and contains crystalline nitrendipine, polyvinylpyrrolidone and sodium laurylsulphate, and to a process for its preparation.

Chemically, nitrendipine is 3-methyl-5-ethyl 2,6-dimethyl-4-(3'-nitrophenyl)-1,4-dihydropyridine-3,5-dicarboxylate of the formula

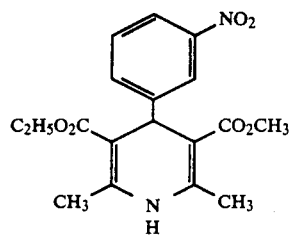

and can be prepared by reacting the ylidene-ketocarboxylic acid ester of the formula

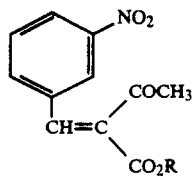

in which
R represents methyl or ethyl, with an enaminocarboxylic acid ester of the general formula

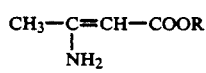

in which
R denotes methyl or ethyl, or by reacting the above ylidene-β-ketocarboxylic acid ester with ammonia or a ketocarboxylic acid of the formula

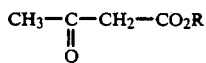

in which R represents methyl or ethyl.

The compound nitrendipine and its antihypertensive action is known (GB-PS No. 1 358 951). Special galenic formulations containing nitrendipine in corprecipitate form (non crystalline) are also known (DE-OS No. 3 142 853).

On the basis of its extremely low solubility of 2 mg/L in aqueous media, the active compound can be dissolved in the amount required to achieve an optimum plasma level only by a special galenic formulation. It is known that the solubility of a sparingly soluble substance is improved by processing larger amounts of auxiliaries. However, since this medicament is to be employed for longterm therapy of hypertension, it is necessary to prepare a small formulation with smaller amounts of auxiliaries, which can be taken without problems.

The invention thus relates to a solid medicament formulation containing 1 part by weight of crystalline nitrendipine, 0.5–1 part by weight of polyvinylpyrrolidone, 0.05–0.5 part by weight of sodium lauryl-sulphate, 1–3 parts by weight of corn starch, 0.5–2 parts by weight of microcrystalline cellulose, 0–2 parts by weight of lactose and 0.01–0.05 part by weight of magnesium stearate.

Polyvinylpyrrolidone with an average molecular weight of 10,000–360,000, in particular 10,000–40,000, can preferably by employed.

The medicament formulation can preferably contain 0.1–0.3 part by weight of sodium lauryl-sulphate.

The unexpected high bioavailability of the inventive formulations, which are of very small size, can be seen by comparing the dissolution rates of an inventive composition (tablet A) which contains sodium laurylsulfate and polyvinylpyrrolidone, against tablets B and C, as can be seen in the following tables 1 and 2.

TABLE 1

| Ingredients and content of different tablets | | | |
|---|---|---|---|
| | Tablet A (inventive tablet) | Tablet B | Tablet C |
| Bay e 5009 | 20,0 mg | 20,0 mg | 20,0 mg |
| Corn starch | 27,8 mg | 17,5 mg | 167,0 mg |
| Avicel (microcrystalline cellulose) | 20,0 mg | 22,6 mg | 48,0 mg |
| Polyvinylpyrrolidone 25 | 10,0 mg | — | — |
| Lactose | — | 16,7 mg | 140,0 mg |
| Sodiumlaurylsulfate | 2,0 mg | — | — |
| Aerosil | — | 2,0 mg | 4,0 mg |
| Tween 80 | — | 1,0 mg | — |
| Magnesiumstearate | 0,2 mg | 0,2 mg | 1,0 mg |
| Total weight | 80,0 mg | 80,0 mg | 380,0 mg |
| Tablet-diameter | 6,0 mm | 6,0 mm | 10,0 mm |

TABLE 2

| Dissolution rate (USP-Paddle; 4000 ml; 0,1 n HCl; n = 6) | | | |
|---|---|---|---|
| time | Tablet A | Tablet B | Tablet C |
| after 30 min. | 26,0% | 5,0% | 20,0% |
| after 60 min. | 31,0% | 8,0% | 23,0% |
| after 120 min. | 32,0% | 9,0% | 31,0% |

The medicament formulation can be prepared in a known manner by aqueous granulation in a planetary mixer or by the fluidized bed method, or by dry granulation by the milling method. Aqueous granulation is preferably carried out, it being easier to control granulation in the fluidized bed via the spraying and the drying conditions in comparison with granulation in the planetary mixer.

Granulation in a planetary mixer

The nitrendipine, corn starch, lactose and microcrystalline cellulose are mixed in the dry state and granulated with a solution of polyvinylpyrrolidone (PVP), sodium lauryl-sulphate and water.

After drying, the granules are sieved and magnesium stearate is added.

EXAMPLE 1

| Nitrendipine | 20 g |
|---|---|
| Corn starch | 27 g |
| Lactose | 9 g |

-continued

| Microcrystalline cellulose | 14.7 g | are mixed in the dry state and the mixture is granulated with a solution of

| PVP (molecular weight 25,000) | 15 g |
| Sodium lauryl-sulphate | 4 g |
| Water | 10 g |

The moist mass is rasped, dried and sieved. After addition of 0.3 g of magnesium stearate, the granules are pressed to tablets containing 20 mg of nitrendipine.

EXAMPLE 2

| Nitrendipine | 10 g |
| Corn starch | 23 g |
| Lactose | 15 g |
| Microcrystalline cellulose | 14.7 g | are mixed in the dry state and granulated with a solution of

| PVP (molecular weight 25,000) | 10 g |
| Sodium lauryl-sulphate | 2 g |
| Water | 10 g |

The moist mass is rasped, dried and sieved. After addition of 0.3 g of magnesium stearate, the granules are pressed to tablets containing 10 mg of nitrendipine.

Granulation in a fluidized bed

The nitrendipine, corn starch, lactose and microcrystalline cellulose are mixed in a fluidized bed and granulated by the spraying method with a solution consisting of polyvinylpyrrolidone, sodium lauryl-sulphate and water.

After drying, the granules are sieved and magnesium stearate is added.

EXAMPLE 3

| Nitrendipine | 20 g |
| Corn starch | 25 g |
| Lactose | 6 g |
| Microcrystalline cellulose | 14.7 g | are mixed in the dry state and granulated with a solution of

| PVP (molecular weight 10,000) | 20 g |
| Sodium lauryl-sulphate | 4 g |
| Water | 10 g |

The moist mass is rasped, dried and sieved. After addition of 0.3 g of magnesium stearate, the granules are pressed to tablets containing 20 mg of nitrendipine.

EXAMPLE 4

| Nitrendipine | 20 g |
| Corn starch | 25 g |
| Lactose | 6 g |

-continued

| Microcrystalline cellulose | 14.7 g | are mixed in the dry state in a fluidized bed and granulated by the spraying method with a solution of

| PVP (molecular weight 25,000) | 20 g |
| Sodium lauryl-sulphate | 4 g |
| Water | 10 g |

When the spraying operation has ended, the granules are dried and sieved. After addition of 0.3 g of magnesium stearate, the finished granules are pressed to tablets containing 20 mg of nitrendipine.

EXAMPLE 5

| Nitrendipine | 10 g |
| Corn starch | 23 g |
| Lactose | 15 g |
| Microcrystalline cellulose | 14.7 g | are mixed in a fluidized bed and a solution of

| PVP (molecular weight 25,000) | 10 g |
| Sodium lauryl-sulphate | 2 g |
| Water | 10 g | is stirred in. The mixture is dried and sieved. After addition of 0.3 g of magnesium stearate, tablets containing 10 mg of nitrendipine are pressed.

EXAMPLE 6

| Nitrendipine | 10 g |
| Corn starch | 26 g |
| Lactose | 17 g |
| Microcrystalline cellulose | 14.7 g | are mixed in a fluidized bed and a solution of

| PVP (molecular weight 40,000) | 5 g |
| Sodium lauryl-sulphate | 2 g |
| Water | 10 g | is stirred in. The mixture is dried and sieved. After addition of 0.3 g of magnesium stearate, tablets containing 10 mg of nitrendipine are pressed.

It will be understood that the specification and examples are illustrative but not limitative of the present invention and that other embodiments within the spirit and scope of the invention will suggest themselves to those skilled in the art.

We claim:

1. A solid medicament formulation comprising 1 part by weight of crystalline nitrendipine, 0.5–1 part by weight of polyvinylpyrrolidone with an average molecular weight of 10,000–360,000, 0.05–0.5 part by weight of sodium laurylsulphate, 1–3 parts by weight of corn starch, 0.5–2 parts by weight of microcrystalline cellulose, 0–2 parts by weight of lactose and 0.01–0.05 part by weight of magnesium stearate.

2. A solid medicament formulation according to claim 1, containing 0.1–0.3 part by weight of sodium lauryl-sulphate.

3. A solid medicament formulation according to claim 1, containing polyvinylpyrrolidone with an average molecular weight of 10,000–40,000.

* * * * *